(12) United States Patent
Pessala et al.

(10) Patent No.: US 10,010,691 B2
(45) Date of Patent: Jul. 3, 2018

(54) BREATHING APPARATUS AND METHOD FOR DETECTING LEAKAGE IN A SAMPLING LINE

(71) Applicant: MAQUET CRITICAL CARE AB, Solna (SE)

(72) Inventors: Tom Pessala, Bromma (SE); Toni Oradd, Stockholm (SE); Kiomars Fathollahzadeh, Jarfalla (SE); Mats Eriksson, Sollentuna (SE)

(73) Assignee: MAQUET CRITICAL CARE AB, Solna (SE)

( * ) Notice: Subject to any disclaimer, the term of this patent is extended or adjusted under 35 U.S.C. 154(b) by 515 days.

(21) Appl. No.: 14/439,957

(22) PCT Filed: Oct. 30, 2013

(86) PCT No.: PCT/EP2013/072716
§ 371 (c)(1),
(2) Date: Apr. 30, 2015

(87) PCT Pub. No.: WO2014/068000
PCT Pub. Date: May 8, 2014

(65) Prior Publication Data
US 2015/0273172 A1 Oct. 1, 2015

Related U.S. Application Data

(60) Provisional application No. 61/720,853, filed on Oct. 31, 2012.

(51) Int. Cl.
*A61M 16/00* (2006.01)
*A61M 16/08* (2006.01)
*A61M 16/10* (2006.01)

(52) U.S. Cl.
CPC ...... *A61M 16/085* (2014.02); *A61M 16/0003* (2014.02); *A61M 16/0051* (2013.01);
(Continued)

(58) Field of Classification Search
CPC ............. A61M 16/00; A61M 16/0027; A61M 16/0003; A61M 16/0051; A61M 16/022;
(Continued)

(56) References Cited

U.S. PATENT DOCUMENTS 6,152,129 A * 11/2000 Berthon-Jones ...... A61M 16/00
128/200.24
6,305,212 B1 10/2001 Drzewiecki
(Continued)

FOREIGN PATENT DOCUMENTS

| EP | 1 961 439 | 8/2008 |
|---|---|---|
| EP | 1 974 763 | 10/2008 |
| WO | WO 88/02890 | 4/1988 |

*Primary Examiner* — Valerie L Woodward
(74) *Attorney, Agent, or Firm* — Fay Kaplun & Marcin, LLP

(57) ABSTRACT

In a breathing apparatus and a method for the operation thereof, a gas monitor monitors at least one gas and includes a pump that controls a sidestream flow from a patient circuit to the gas monitor via a sampling line having a first end connectable to the gas monitor and a second end connectable to the patient circuit. At least one pressure sensor measures a pressure at the sidestream gas monitor and provides a first pressure signal indicative of the measured pressure. A processor determines if a leakage is occurring in the sampling line based on the pressure signal.

19 Claims, 3 Drawing Sheets

(52) U.S. Cl.
CPC ...... *A61M 16/0069* (2014.02); *A61M 16/024* (2017.08); *A61M 16/0833* (2014.02); *A61M 16/0883* (2014.02); *A61M 16/104* (2013.01); *A61M 16/0057* (2013.01); *A61M 16/0858* (2014.02); *A61M 2016/0027* (2013.01); *A61M 2205/15* (2013.01); *A61M 2205/3334* (2013.01)

(58) Field of Classification Search
CPC ........ A61M 16/024; A61M 16/0841–16/0858; A61M 2016/102–2016/1035; A61M 2016/0027
See application file for complete search history.

(56) References Cited

U.S. PATENT DOCUMENTS

| | | | | |
|---|---|---|---|---|
| 7,556,039 B1* | 7/2009 | Pierry | .................. | A61B 5/0836 128/204.18 |
| 8,033,280 B2 | 10/2011 | Heinonen | | |
| 2002/0014240 A1* | 2/2002 | Truschel | ................ | A61M 16/00 128/204.22 |
| 2007/0107728 A1* | 5/2007 | Ricciardelli | ........... | A61B 5/087 128/204.21 |
| 2008/0114223 A1* | 5/2008 | Pierry | .................... | A61B 5/083 600/301 |
| 2008/0202526 A1* | 8/2008 | Heinonen | ......... | A61M 16/0051 128/204.22 |
| 2008/0236583 A1 | 10/2008 | Tigerstedt | | |
| 2010/0101574 A1* | 4/2010 | Bassin | .............. | A61M 16/0051 128/204.21 |
| 2010/0147303 A1* | 6/2010 | Jafari | ................ | A61M 16/0051 128/204.23 |
| 2010/0186741 A1* | 7/2010 | Aylsworth | ........ | A61M 16/0051 128/203.29 |
| 2011/0209703 A1* | 9/2011 | Usuda | ............... | A61M 16/0051 128/204.22 |
| 2012/0136325 A1* | 5/2012 | Allen | .................. | A61M 1/0031 604/319 |
| 2014/0216451 A1* | 8/2014 | Jaffe | ................ | A61M 16/0051 128/202.22 |

* cited by examiner

BREATHING APPARATUS AND METHOD FOR DETECTING LEAKAGE IN A SAMPLING LINE

BACKGROUND OF THE INVENTION

1. Field of the Invention

This invention pertains in general to the field of medical devices. More particularly, the invention relates to breathing apparatuses. Even more particularly, the invention relates to detection of leakage in a sampling line of a breathing apparatus such as an anaesthesia apparatus.

2. Description of the Prior Art

A side stream gas flow is provided in these sampling lines from a main stream gas channel in the breathing apparatus. The gas monitors are thus able to measure a concentration of one or more gases and/or identifying presence of a specific gaseous component in the gas channel. Such measurements are for instance useful for controlling the breathing apparatus and to maintain patient safety. It is desired to detect leakage in such sampling lines, in the rare case such leakage should occur.

There are some known systems for detecting leakage in side stream sampling lines to gas monitors.

In U.S. Pat. No. 8,033,280 A, a method is disclosed for detection of a sampling gas line leak while measuring patient breathing gas, wherein at least two measured gas concentrations are used in order to determine a leakage.

In published application number US 2008/0236583 A, patient circuit pressure changes are correlated to measured sampling gas concentrations and a leakage may thus be determined based on said correlation. However, this method is rather complicated and prone to errors due to its complexity and the number of components involved.

Systems and methods, such as in the aforementioned two documents, for detecting leakage in a sampling line based on measured gas concentrations and comparisons to expected patient gas concentrations require a patient to be connected to be able to establish if there is a leakage or not. Hence, such systems and methods cannot be implemented without connected patient, for instance during a pre-use check of a breathing apparatus.

There is a need for an improved or alternative solution to detect leakage in a sampling line of a gas monitor. It is desired that a system and/or method is provided, which provide a reliable and accurate and/or robust leakage detection.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an apparatus and a method according to the appended patent claims.

According to aspects of the invention, a method and an apparatus are disclosed, whereby it can be determined if a leakage of a sampling line is occurring.

A pressure sensor or pressure measurement is provided at a gas monitor for detecting a leakage, such as a leakage of a sampling line.

The leakage detection of the disclosure is based on the fact that during a leakage the negative pressure applied by a sampling pump of the gas monitor will rise towards ambient pressure. Alternatively, or in addition, the disclosure is based on the fact that during a leakage the amplitude of a breathing circuit pressure, i.e. the maximum difference during a breathing cycle, will decrease in the leaking sampling line. In the extreme, if a sampling line or hose is disconnected or if a sampling line or hose is severed off, no pressure variation will be detected at all in the sidestream section still connected to the gas monitor input, as the sampling pump of the gas monitor will draw ambient air at ambient pressure only.

With a pressure sensor at the gas monitor for detecting a leakage, i.e. by utilizing a pressure sensor, a direct measurement can be obtained, wherein pressure is compared to pressure. The pressure sensor may already be present in or at the monitor. Alternatively, or in addition, a separate pressure sensor may be provided for the purpose of leakage detection. Thus, a straight forward measurement is performed and therefore a more reliable, more accurate and/or a more robust leakage detection may be made.

According to the invention, a breathing apparatus is provided that has a gas monitor for monitoring at least one gas. The gas monitor includes a pump for controlling a sidestream flow to the gas monitor. The sidestream flow is connectable to a mainstream of a patient circuit, e.g. at Y-piece. The breathing apparatus further has a sampling line for the sidestream flow. The sampling line has a first end and a second end. The first end is connectable to the gas monitor and the second end is connectable to the patient circuit, preferably at a Y-piece of the patient circuit. Furthermore, the breathing apparatus has at least a first pressure sensor for measuring a pressure at the sidestream gas monitor. The pressure sensor provides in operation a first pressure signal for the pressure at the gas monitor. Moreover, the breathing apparatus has a processing unit operative to determine if a leakage of the sampling line is occurring based on at least the first pressure signal.

According to another aspect of the invention, a method in a breathing apparatus is provided, that includes sampling gas from the patient circuit with a sampling line. The method further includes controlling a sidestream flow to a gas monitor, connected to the sampling line. Furthermore, the method includes monitoring the gas with the gas monitor. Moreover, the method includes measuring a pressure at the sidestream gas monitor. The method also includes providing a first pressure signal for the pressure. In addition, the method includes determining if a leakage of the sampling line is occurring, based on at least the pressure signal. A control unit may be configured to perform the method.

In the present context, the term "leakage of a sampling line" includes disconnection of a sampling line such that the gas monitor samples ambient air. Disconnection may occur for instance if the sampling tube is drawn out of a connection with the gas monitor. Disconnection may also occur when the sampling line, such as a hose or a tube, is worn or cut off along its length, which should of course be avoided, but might occur in some clinical situations. In the latter case, a length of the sampling line may still be connected to the inlet of the gas monitor.

In the present context the term "at a gas monitor" means spatially at the gas monitor, i.e. at least in close vicinity to the gas monitor, like inside a housing of a gas monitor or at an inlet for a sampling line of a gas monitor.

In the present context the term "leakage" refers to leakage of a sampling line, such as a hose or a tube, including partial leakage to ambient environment, such as by perforation or partial disconnection of the tube, as well as total leakage, such as by disconnection of the sampling tube, or a tube worn or cut off along its length, leaving only a section of the tube connected to a gas monitor with an open end to ambient environment.

DESCRIPTION OF THE PREFERRED EMBODIMENTS

Figure 1:
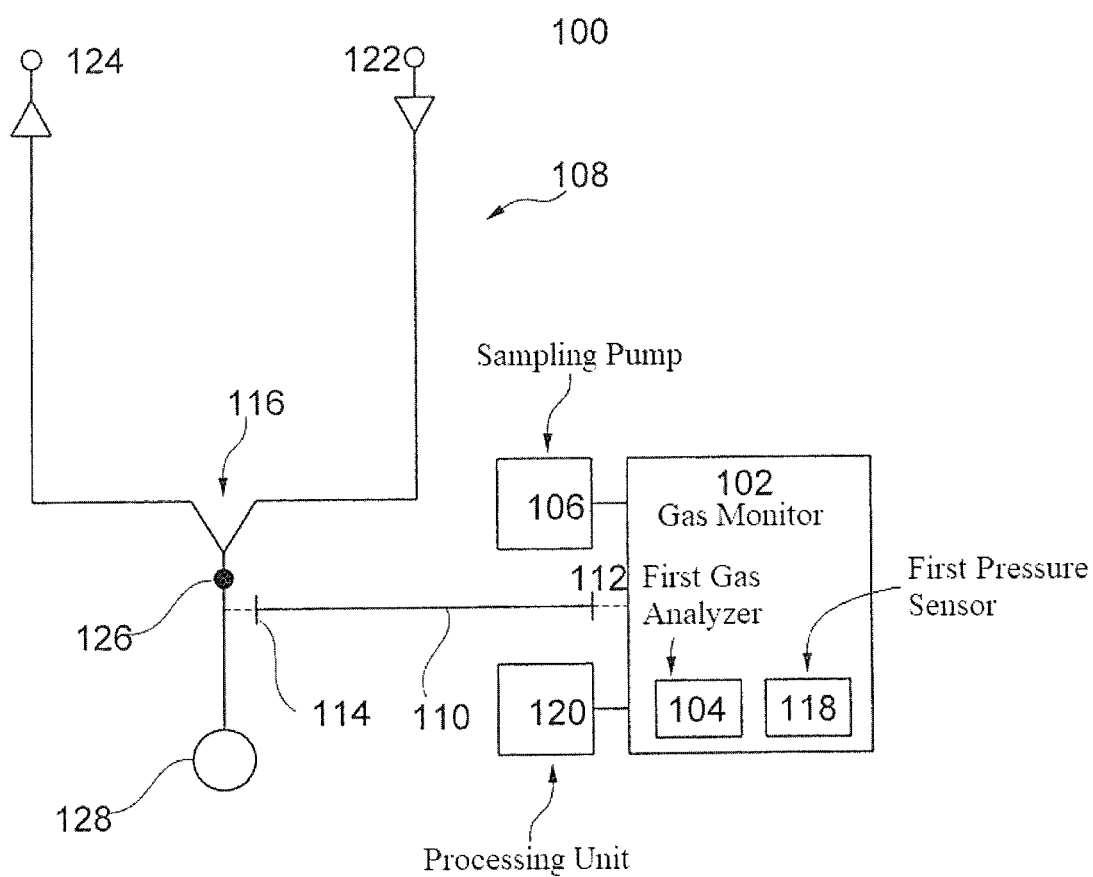
FIG. 1 is an illustration of a breathing apparatus.

Specific embodiments of the disclosure will now be described with reference to the accompanying drawings. The following description focuses on an embodiment of the present disclosure applicable to a breathing apparatus and in particular to an anaesthesia apparatus. This disclosure may, however, be embodied in many different forms and should not be construed as limited to the embodiments set forth herein; rather, these embodiments are examples provided so that this disclosure will be thorough and complete, and will fully convey the scope of the disclosure to those skilled in the art. Thus, it will be appreciated that the disclosure is not limited to a breathing apparatus but may be applied to many other breathing apparatuses, such as intensive care ventilators, preferably with anaesthesia capabilities. The terminology used in the detailed description of the embodiments illustrated in the accompanying drawings is not intended to be limiting of the disclosure. In the drawings, like numbers refer to like elements.

In FIG. 1 a portion of an anesthetic breathing apparatus 100 is illustrated including an embodiment of the present disclosure. The breathing apparatus is for instance one of the type as described in WO2009/062550A1, there including two sidestream gas analyzers 200, 210 described in relation to FIGS. 1-3 thereof; or described in WO2007/071756A1, there including a sidestream gas analyzer 23; or described in WO2009/062540A1, there including a sidestream gas analyzer 23 described in relation to FIGS. 1 and 2 thereof; or described in WO2010/081914AI, there including a sidestream gas analyzer 170 described in relation to FIGS. 1,3 6 and 7 thereof. WO2009/062550A1, WO2007/071756A1, WO2009/062540AI, and WO2010/081914AI are disclosures of the same applicant as the present application and are incorporated herein by reference in their entirety, but in particular the aforementioned passages, for all purposes.

As seen in FIG. 1, the breathing apparatus 100 comprises a gas monitor 102 for monitoring at least one gas. The gas monitor may be a first gas analyzer 104 or may comprise a first gas analyzer 104. The gas monitor includes a pump 106 for controlling a sidestream flow to the gas monitor 102. The sidestream flow is connectable to a mainstream of a patient circuit or patient breathing circle 108 via a sampling line 110. A patient 128 may be connected to the patient circuit 108. However, in some embodiments, during the determining of if a leakage of the sampling line is occurring, the patient 128 may be disconnected from the patient circuit 108. A patient may for instance be disconnected during a pre-use check procedure of the breathing apparatus 100.

The sampling line 110 has a first end 112 and a second end 114. The first end 112 is connectable to the gas monitor 102 and the second end 114 is connectable to the patient circuit 108, preferably at a Y-piece 116 of the patient circuit 108. In normal operation of the apparatus 100, the ends 112, 114 are connected accordingly in a leakage free manner, e.g. via Luer connectors known in the art. However, leakage may occur, as already discussed above.

Furthermore, the breathing apparatus 100 comprises at least a first pressure sensor 118 for measuring a pressure at the sidestream gas monitor 102. Pressure sensor 118 is arranged such that it, in operation of the breathing apparatus 100, is providing a first pressure signal for the pressure at the sidestream gas monitor 102, i.e. preferably downstream (gas flow direction in the sampling line 110 towards the gas monitor 102) the first end 112 of the sampling line 110.

Pressure sensor 118 is preferably arranged at gas monitor 102 to provide a compact unit. Pressure sensor 118 may in other examples be arranged at other suitable locations in the breathing apparatus 100, e.g. connected to the pressure sampling or measurement location at the gas monitor via a suitable conduit.

Moreover, the breathing apparatus 100 comprises a processing unit 120 operative to determine if a leakage of the sampling line is occurring based on at least the first pressure signal. The processing unit 120 is connected to the first pressure sensor 118 directly or via other units for receiving the first pressure signal. Processing unit 120 may in examples be part of a processing unit of the breathing apparatus or of another processing unit in the system, such as a processing unit of the gas monitor 102 (not shown). Processing unit 120 is configured to execute program code, for instance stored on a computer readable medium (not shown) accessible by the processing unit 120.

In some embodiments, the pressure sensor 118 is positioned at the gas monitor 102. As an example, the pressure sensor 118 may be integrated with the gas monitor 102. Alternatively, the pressure sensor 118 is a separate unit, which is connectable to the pressure sampling location at the gas monitor 102.

The first pressure sensor 118 measures the side stream pressure at the gas monitor 102. This pressure is influenced by the breathing circuit pressure and the sampling pump 106, as can be seen more in detail in FIGS. 3 and 4. Thus, the measured pressure, measured with the first pressure sensor 118, is indicative of and/or proportional to the pressure in the breathing circuit. The relationship between the pressure measured with the first pressure sensor and the pressure in the breathing circuit may be described by a formula. The breathing circuit pressure varies during the inspiratory and expiratory phases as schematically described in FIGS. 3 and 4.

The sampling leakage detection of the disclosure is based on the fact that during a leakage the negative pressure applied by the sampling pump 106 will rise towards ambient pressure, and the fact that during a leakage the amplitude of the breathing circuit pressure, i.e. the maximum difference during a breathing cycle, will decrease in the sampling line. If a sampling hose is disconnected or if a sampling hose is severed off, no pressure variation will be detected at all in the sidestream and the sampling pump will draw ambient air at ambient pressure only.

Figure 3:
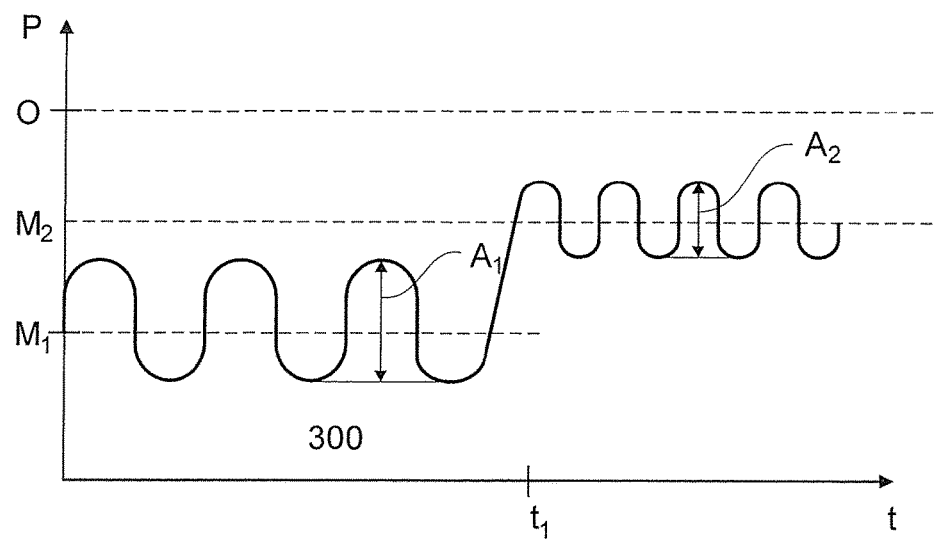
FIG. 3 is an illustration of a pressure signal.
Figure 4:
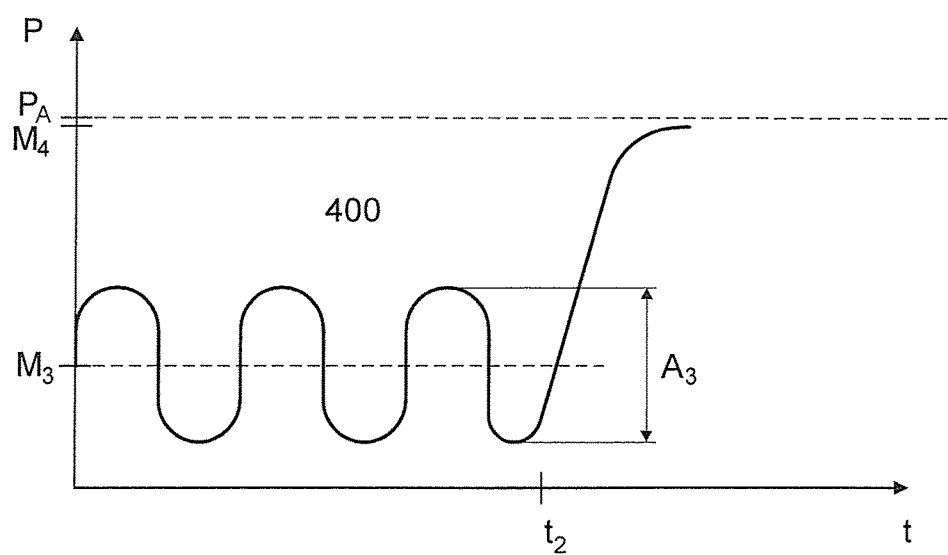
FIG. 4 is an illustration of another pressure signal.

FIG. 3 and FIG. 4 are illustrations of examples of typical pressure signals 300, 400 of the pressure sensor 118.

From FIG. 3, it can be seen that the pressure signal 300 has a first amplitude $A_1$ and a first mean value $M_1$ before time $t_1$. At time $t_1$ a leakage occurs, such as because the sampling line 110 has been perforated. Thereafter the pressure signal 300 has a second amplitude $A_2$ and a second mean value $M_2$. Thus, it is possible to detect a leakage from the pressure signal 300 from the difference in amplitude (delta $A_1$ to $A_2$) and/or the difference in mean value (delta $M_1$ to $M_2$). From FIG. 3 a zero level, indicated with 0, can be seen. Thus, it is clear that the levels $M_1$ and $M_2$ are below zero.

Similarly, from FIG. 4, it can be seen that the pressure signal 400 has a third amplitude $A_3$ and a third mean value $M_3$ before time $t_2$. However, at time $t_2$ a leakage occurs, such as because a hose of the sampling line has been disconnected. Thereafter the pressure signal 400 levels to a fourth mean value $M_4$, which is close to the ambient pressure $P_A$, but there is no longer any amplitude in the pressure signal 400. Thus, it is possible to detect a leakage or a disconnected hose from the pressure signal 400 by determining a difference in amplitude, the lack of an amplitude, the difference in mean value and/or the similarity of the pressure signal 400 to the ambient pressure. A degree of leakage may be detected accordingly, if so desired. Depending on the degree of leakage, suitable action may be taken in the breathing apparatus, including notification to an operator in various degrees of seriousness, if so desired.

Note that the indicated sinus-shaped variations/pressure swings due to the inspiratory and expiratory phases in FIGS. 3 and 4 are schematic illustrations only. Such variations may not only occur with connected patient 128, but also during a pre-use check, e.g. with connected inspiratory and expiratory tubing and/or test lung at the Y-piece.

In some embodiments, the processing unit 120 is configured to determine an average pressure over a time period. The time period may be at least one inspiratory phase and/or at least one expiratory phase. Preferably, the time period is at least one or several expiratory phases and one or several inspiratory phases. Thus, an average value of the pressure can be obtained. The averaged value may be utilized by the processing unit 120 of the breathing apparatus 100 for determining if a leakage of the sampling line 110 has occurred. The determining is then based on a variation in the averaged measured pressure, such as described above with reference to FIGS. 3 and 4.

In some embodiments, a reference pressure is predetermined. As an example, such a reference pressure may be an ambient pressure. Alternatively or in addition, a reference amplitude for the first pressure signal is predetermined.

In this manner, detection of a leakage may be made by comparing measured pressures to the reference pressure.

As an alternative, the reference pressure and/or the reference amplitude are measured with the first pressure sensor 118 prior to or during the determining of if a leakage has occurred. Preferably, the reference pressure and/or the reference amplitude are measured at a system check out (pre-use check), at zeroing or prior to starting determining if a leakage of the sampling line 110 is occurring.

A system check out, i.e. a pre use check, is normally carried out prior to the use of the breathing apparatus. During the pre-use check, the system is checked in order to make sure that the all checkable components are working correctly, including a leakage free sampling line 110. A patient is not connected to the breathing apparatus during the pre-use check, and a test lung or similar arrangements may be used instead. During pre-use check an operational check of various functions of the apparatus 100 is performed, e.g. controlled by processing unit 120. For instance, a suitable test is performed to check for leakage in the system to ensure that the pneumatic system of the apparatus 100 and/or connected tubing, including for instance the patient circuit 108, patient tubes, or sampling line 110. A leakage may thus be detected and removed during a pre-use check before a patient is connected to apparatus 100. Methods to detect leakage during a pre-use check include for instance to detect a sinking pressure in a static system without gas flow, a deviation of metered and measured fresh gas concentrations, etc. Such pre-use check may include obtaining measurements of system characteristics, including the aforementioned reference pressure and/or the reference amplitude. Moreover, pressure drop properties of a connected sampling line may be determined during pre-use check, which measured pressure drop characteristics are then used to reliably determine a leakage of the sampling line. A method to detect a sampling line leakage described herein may be performed during such pre-use check.

In some embodiments, the breathing apparatus 100 has at least a second pressure sensor and may have further pressure sensors 122, 124, 126 for measuring the breathing circuit pressure, i.e. the inspiratory pressure during an inspiratory phase and the expiratory pressure during an expiratory phase. This second pressure sensor 122, 124, 126 is preferably located at the Y-piece 116 or at an expiration output and/or an inspiration output of the breathing apparatus 100 and/or the patient circuit 108.

In some embodiments, the reference pressure and/or the reference amplitude is based at least on a pressure signal provided by the second pressure sensor 122, 124, 126. The second pressure sensor 126 is preferably positioned at the Y-piece 116.

Alternatively, or in addition, the reference pressure and/or the reference amplitude is based at least on a second and a third pressure sensor 122, 124, one being located at an expiration output and the other one being located at an inspiration output.

As mentioned above, the reference pressure and/or the reference amplitude are preferably measured during a pre use check of the breathing apparatus. However, the reference pressure and/or the reference amplitude may alternatively and/or in addition be regularly measured or updated with a certain time interval during operation of the breathing system 100. As an example, the pump 106 may temporarily be turned off for a short period of time during operation of the breathing apparatus. During this short period of time, variations in pressure may be measured. The measured pressure variations can then be compared to previously made measurements and this comparison may then give information about whether the resistance of the system has changed or not. If the resistance of the system has changed, then also the degree of filtration and thus time constants of the system has changed. Thus, from information of changes in pressure variations, an indication of how the reference pressure and/or the reference amplitude may have changed can be obtained. In this manner, a compensation may be made for previously determined reference pressures and the leakage detection is made more robust.

In some embodiments the second pressure sensor 122, 124, 126 is provided to measure a reference pressure. In these embodiments the reference pressure is preferably measured at the Y-piece 116. Alternatively, the second pressure sensor 122, 124 and the third pressure sensor 122, 124 are provided to measure a reference pressure. In these embodiments the reference pressure is preferably measured at an expiration output and an inspiration output.

In some embodiments, the processing unit 120 is configured to calculate an amplitude of the measured pressure as a difference between a maximum value and a minimum value of the pressure during a breathing cycle. The processing unit 120 is configured to compare the amplitude of the measured pressure to a corresponding reference amplitude for determining of if a leakage is occurring. The corresponding reference amplitude may be determined by input from the second pressure sensor related to breathing patterns of a ventilated patient. Changes in patient pressures between a maximum value and a minimum value of the patient pressure during a breathing cycle provide for a readily available reference during operation of the breathing apparatus.

Alternatively, an adjusted amplitude may be calculated as a mean value of the measured pressure during the inspiratory phase minus a mean value of the measured pressure during the following expiratory phase. The processing unit 120 is then configured to compare the adjusted amplitude to a corresponding reference amplitude. The corresponding reference amplitude may be determined by input from the second pressure sensor related to breathing patterns of a ventilated patient. Changes in patient pressures related to the inspiratory phase and the following expiratory phase during a breathing cycle provide for a readily available reference during operation of the breathing apparatus.

Alternatively, or in addition, mean values over a plurality of subsequent breathing cycles may be applied in the afore described manner related to a single breathing cycle, but for instance as a moving average.

In this manner, a leakage of the sampling line 110 is reliably detectable based on measured values related to the breathing cycle of a patient ventilated by the breathing apparatus 100.

In some examples the processing unit 120 is configured to determine if gas concentrations, such as oxygen, carbon dioxide, nitrous oxide and/or anesthetic agents, have been changed relative a previous concentration thereof. The processing unit 120 is thereafter determining if a leakage has occurred based on if a change of the gas concentrations is determined and if a deviation in the measured pressure from an expected pressure, such as a variation in the averaged measured pressure has been determined. The determining of if a leakage has occurred may also be based on further criteria. By basing the leakage detection on further criteria, a more accurate detection may be obtained.

In some examples, the pumping velocity of the pump 106 may be used alternatively or additionally to the first pressure as a criterion or a further criterion for determining if a leakage has occurred. For instance, a duty cycle of the pump 106 or another parameter indicative of the pumping velocity of the pump 106 is then continuously measured. The determining of if a leakage has occurred may be based on detection of a change relative a previous value in the measured duty cycle or in the parameter indicative of the pumping velocity. This example may be implemented without additional components in a gas monitor. The processing unit 120 is in the example configured to detect leakage in the sampling line based on variations in the pumping velocity of the pump 106.

In some embodiments the gas monitor 102 of the breathing apparatus 100 comprises an analyzer, such as the first gas analyzer 104. The analyzer may be a portable gas analyzer. Such a portable gas analyzer is used for identifying and/or determining at least one gas and/or its concentration. The gas monitor 102 of the breathing apparatus 100 may also comprise further gas analyzers. The different gas analyzers may then be utilized for different purposes. Several sampling lines may be present and any leakage related to each sampling may be detected as described herein.

In accordance with the invention, a degree of leakage in a sampling line may be detected. In some embodiments the determining of if a leakage of the sampling line 110 is occurring includes determining if there is a through-hole or a perforation of a hose of the sampling line 110. The location of the leakage may be determined, including determining a location of a through-hole or a perforation in the hose. In some examples, the determining of if a leakage of the sampling line 110 is occurring includes determining if a hose of the sampling line is entirely disconnected. Reading the disclosure, the skilled person will be able to implement the detection of a degree of leakage and/or the leakage location based on the measured pressure signal.

Figure 2:
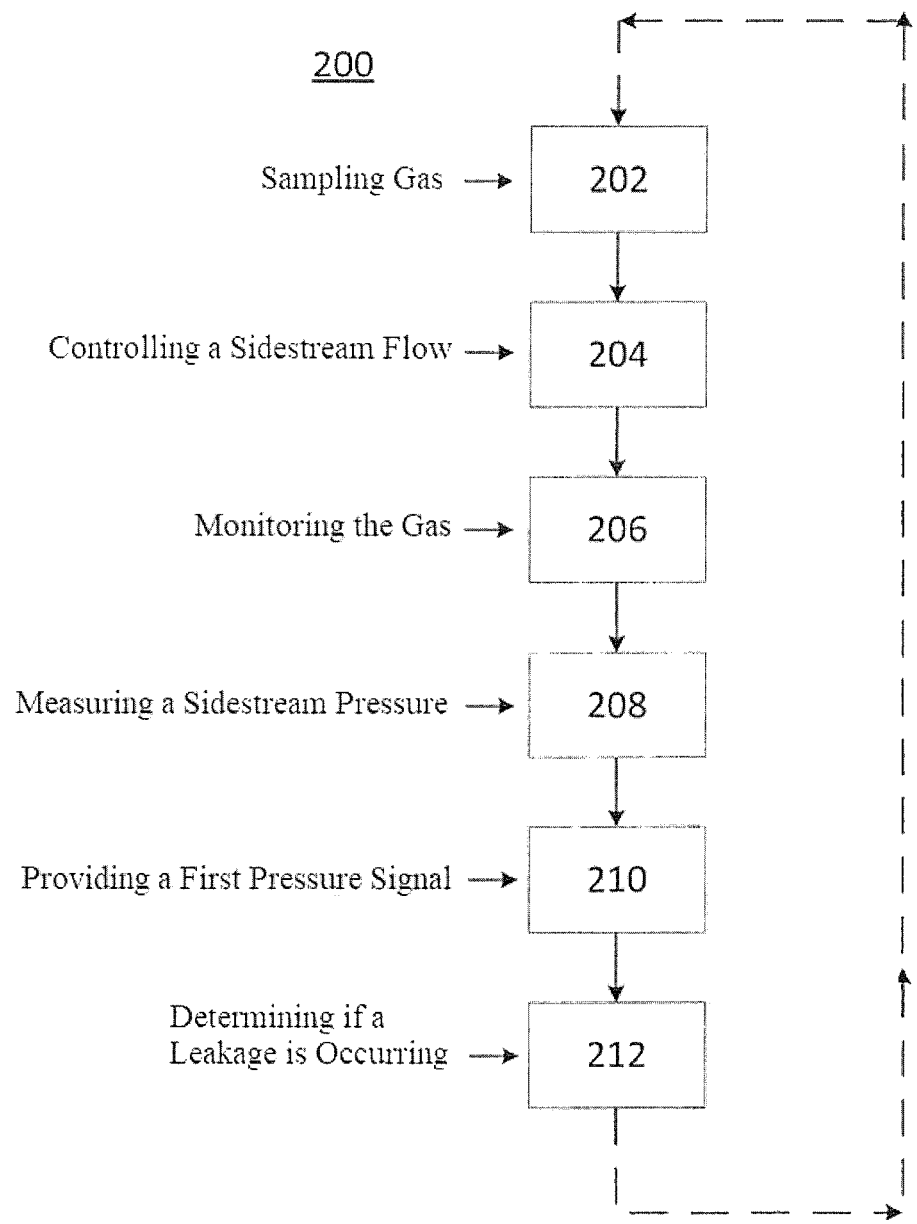
FIG. 2 is an illustration of some steps in a method according to the disclosure.

In FIG. 2 some steps of a method 200 for detecting leakage at a sampling line 110 in a breathing apparatus 100 are illustrated, including an embodiment of the present disclosure.

The method 200 includes sampling 202 gas or gases from a patient circuit 108 with a sampling line 110. The method also includes controlling 204 a sidestream flow to a gas monitor 102, e.g. via a pumping velocity of a pump 106. The gas monitor 102 is connected or connectable to the sampling line 110. Furthermore, the method 200 comprises monitoring 206 the gas with the gas monitor 102. Moreover, the method 200 comprises measuring 208 a sidestream pressure at the sidestream gas monitor 102. In addition, the method 200 comprises providing 210 a first pressure signal for the sidestream pressure. The method 200 also comprises determining 212 if a leakage of the sampling line 110 is occurring, based on at least the first pressure signal. The method 200 may be implemented as a computer program for processing by a computer. The different steps of the method are then implemented as code segments or instructions for execution by a processing unit 120. The code segments or instructions are preferably stored on a computer readable medium (not shown), such as a memory of the breathing apparatus or gas monitor. Furthermore, the method may also be implemented as a system with hardware units for the different steps. The steps of the method may be repeated, such as for monitoring occurrence of a leakage during operation of the breathing apparatus 100 continuously.

The method 200 may also include further steps. In some embodiments, the method 200 also includes determining a reference pressure. The reference pressure may be an ambient pressure. Alternatively, the reference pressure may be an average of the first pressure signal calculated prior to the start of determining if a leakage is occurring.

In some embodiments, the method also includes determining, alternatively or in addition to the reference pressure, a reference amplitude of the first pressure signal prior to determining if a leakage is occurring. An average of the first pressure signal is then compared to the reference pressure for the determining of if a leakage is occurring. Alternatively, or in addition, an amplitude of the measured pressure is compared to the reference amplitude for the determining of if a leakage is occurring.

The amplitude may be determined as a difference between a maximum pressure and a minimum pressure during a breathing cycle from said first pressure signal.

In some embodiments, a first includes average is used for averaging the signal of the first pressure sensor 118. In addition, a second running average may be used. The second running average may be the same as the first running average, but with an offset in time, i.e. the second running average operates on the same pressure signal and with the same operations as the first running average, but with values of the pressure signal that where sampled at different time instances. Alternatively, the second running average operates on a second pressure signal provided by a second pressure sensor 122, 124, 126.

The average of the second pressure sensor 122, 124, 126 may be used as a reference pressure, which the average of the first pressure sensor 118 is compared to in order to determine if a leakage is occurring.

Hence, in an example, the difference of maximum and minimum pressure for both the pressure signal from the first pressure sensor 118 and a patient pressure signal from one of the second pressure sensors 122, 124, 126 is calculated by the control unit for every breath. If the delta pressures between those pressure differences is too big a sample tube leakage alarm can be raised. In case a sampling tube with high pressure drop is connected then the alarm limit may be reduced to avoid false alarms, compared to sampling tubes with low pressure drop. For instance, a "high pressure drop" threshold for a sampling tube at operation with a defined pump flow rate may a pressure drop higher than 42 hPa. A normal pressure drop may be in the range of 35-40 hPa. The sampling tube pressure drop may be measured during pre-use check, as elucidated above, and stored as a pressure drop value in a memory unit (not shown) accessible by the control unit for sampling line leakage or disconnection detection.

The control unit may then apply an adapted leakage alarm limit, in dependence of the sampling line pressure drop value stored in the memory. The control unit may alternatively, or in addition be configured to adapt the leakage alarm limit to currently selected expiration times.

As an example, an alarm may be sent if the amplitude of the first pressure sensor 118 has a value below a threshold value X % compared to the amplitude of the pressure in the breathing circuit.

X % may have a maximum value less than 100%, such as 80%, for normal operation of the leakage alarm.

The maximum value for X % may be selected for expiration times of a pre-selected length, e.g. 1.1 seconds. For shorter expiration times, the value for X % may be reduced down to a minimum value for X %, such as 20%.

Hence, in some embodiments, an alarm is sent to an operator if a leakage is detected.

In order to avoid unnecessary false alarms, a leakage alarm may be sent to an operator upon lapse of a certain time of a detected leakage situation being present. For instance, a leakage situation has to pertain for at least a number of breaths, such as 2 breaths or 5 breaths, and/or a minimum time has to have elapsed, such as 4 seconds or 10 seconds.

The leakage alarm can be active or operator activated in automatic ventilation modes and manual ventilation mode of the breathing apparatus 100. In some operational modes of the breathing apparatus 100, such as when an additional Fresh Gas Outlet is operator activated, the leakage alarm may be automatically disabled or operator disabled.

A disconnection of the sampling tube detected may be related to a disconnection of the sampling tube at a water trap of the gas monitor. The detection of a complete disconnect of a sampling tube at a water trap is in an example detected by processing unit 120 when a) the maximum patient pressure of the last breath is less than a first pre-determined threshold, such as 10 cmH2O, and b) the difference of maximum and minimum patient pressure of the last breath is less than a second pre-determined threshold, such as 5 cmH2O, and c) the maximum momentary O2 concentration of the last breath is close to atmospheric O2 concentration, such as less than 23%.

An alarm for disconnection of the sampling tube at the water trap may for instance be provided to the user if the disconnect situation is detected, such as according to the example above, for at least a pre-determined number of breaths, such as 2 breaths, in a row, and a minimum pre-determined time of disconnection detection, such as 4 s has elapsed.

Zeroing of the gas monitor may inhibit activation criteria of a sample line disconnect alarm, e.g. for 30 seconds. In addition, or alternatively, an ongoing high airway pressure alarm and a gas monitor occlusion alarm may inhibit alarm activation of a sample line disconnect alarm.

The present disclosure has been described above with reference to specific embodiments. However, other embodiments than the above described are equally possible within the scope of the disclosure. Different method steps than those described above, may be provided within the scope of the disclosure. The different features and steps of the disclosure may be combined in other combinations than those described. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

We claim as our invention:

1. A breathing apparatus comprising:
   a gas monitor monitoring at least one gas, including a pump controlling a sidestream flow from a patient circuit to said gas monitor via a sampling line having a first end being connectable to said gas monitor and a second end being connectable to said patient circuit;
   a first pressure sensor that measures a first pressure at said gas monitor, and provides a first pressure signal indicative of said first pressure;
   a second pressure sensor configured to measure a second pressure from the patient circuit, and provides a second pressure signal indicative of said second pressure; and
   a processing unit, wherein the processing unit is configured to determine if a leakage of said sampling line is occurring based on:
   an amplitude of said first pressure signal; and
   one of (i) a predetermined reference amplitude and (ii) a measured reference amplitude of said first pressure signal based on the second pressure signal.

2. The breathing apparatus of claim 1, wherein:
   the first pressure comprises a sidestream pressure, said sidestream pressure being indicative of a breathing circuit pressure when said sampling line is connected at its ends.

3. The breathing apparatus of claim 1, wherein:
   said processing unit is configured to determine an average first pressure from said first pressure signal over a time period; and
   said processing unit is configured to determine if a leakage of said sampling line has occurred based on a variation in said averaged first pressure.

4. The breathing apparatus of claim 3, wherein said first pressure sensor measures a reference pressure prior to determining if a leakage is occurring, during at least a breathing cycle, at least one inspiratory phase or at least one expiratory phase.

5. The breathing apparatus of claim 3, wherein said processing unit is configured to determine if gas concentrations have been changed relative to a previous concentration thereof, and to determine if a leakage has occurred when a change of said gas concentrations has been detected and when a variation in said averaged first pressure is determined.

6. The breathing apparatus of claim 1, wherein said processing unit is configured to calculate an amplitude of said first pressure as a difference between a maximum value and a directly preceding or a directly succeeding minimum value of said second pressure, and wherein said processing unit is configured to compare said amplitude of said first pressure to said predetermined reference amplitude or said measured reference amplitude for said determining of if a leakage is occurring.

7. The breathing apparatus of claim 1, wherein said processing unit is configured to calculate a difference between a maximum pressure and a minimum pressure during a breathing cycle from said first pressure signal; and wherein said processing unit is configured to continuously compare said calculated difference to a previously calculated difference for determining if a leakage is occurring.

8. The breathing apparatus of claim 1, wherein a duty cycle of said pump is continuously measured, and wherein determining if a leakage has occurred is based on detection of a change relative to a previous value in said measured duty cycle.

9. The breathing apparatus of claim 1, wherein determining if a leakage of said sampling line is occurring includes determining if a hose of said sampling line is disconnected, determining if there is a through-hole or a perforation of a hose of said sampling line.

10. The breathing apparatus of claim 1 wherein said processing unit is configured to determine if said leakage of said sampling line is occurring based further on a predetermined reference pressure.

11. The breathing apparatus of claim 10 wherein said reference pressure is an ambient pressure.

12. The breathing apparatus of claim 1 wherein said processing unit is configured to determine if said leakage of said sampling line is occurring based further on a reference value that is measured in a pre-use check of said breathing apparatus, said reference value being a reference pressure of said first pressure signal.

13. The breathing apparatus of claim 12 wherein said reference pressure is an ambient pressure.

14. The breathing apparatus of claim 1 wherein said second pressure sensor is situated at a location selected from the group consisting of an expiration output, an inspiration output, and a y-piece separation between an inspiration line and an expiration line.

15. The breathing apparatus of claim 1, wherein said processing unit is configured to determine if said leakage of said sampling line is occurring based further on a pressure drop of said sampling line, determined in a pre-use check.

16. A method in a breathing apparatus comprising:
sampling gas from a patient circuit with a sampling line;
controlling a sidestream flow to a gas monitor, connected to said sampling line;
monitoring said gas with said gas monitor;
measuring a first pressure at said sidestream gas monitor;
providing a first pressure signal for said first pressure by means of a first pressure sensor;
determining a reference amplitude by means of a second pressure sensor;
comparing an amplitude of said first pressure signal to said reference amplitude; and
determining if a leakage of said sampling line is occurring based on said comparison between said amplitude of said first pressure signal and said reference amplitude.

17. The method of claim 16, further comprising:
determining a reference pressure, prior to the start of determining if a leakage is occurring; and
comparing an average of said first pressure signal with said reference pressure for said determining of if a leakage is occurring.

18. The method of claim 17, further comprising:
determining a difference between a maximum pressure and a minimum pressure during a breathing cycle from said first pressure signal; and
continuously comparing said difference to a previously calculated difference for determining if a leakage is occurring.

19. The method of claim 16, wherein said method is performed during a pre-use check of the breathing apparatus without a connected patient.

* * * * *